US006365342B1

(12) United States Patent
Wakamiya

(10) Patent No.: US 6,365,342 B1
(45) Date of Patent: Apr. 2, 2002

(54) METHODS FOR DETECTING ANTI-VIRAL ACTIVITY OF CALCIUM-DEPENDENT LECTINS

(75) Inventor: Nobutaka Wakamiya, Ibaraki (JP)

(73) Assignee: Fuso Pharmaceutical Industries, Ltd., Osaka (JP)

(*) Notice: Subject to any disclaimer, the term of this patent is extended or adjusted under 35 U.S.C. 154(b) by 0 days.

(21) Appl. No.: 09/029,156

(22) PCT Filed: Jan. 25, 1996

(86) PCT No.: PCT/JP96/00173

§ 371 Date: Aug. 3, 1998

§ 102(e) Date: Aug. 3, 1998

(87) PCT Pub. No.: WO97/07210

PCT Pub. Date: Feb. 27, 1997

Related U.S. Application Data

(63) Continuation-in-part of application No. 09/011,375, filed as application No. PCT/JP95/02035 on Oct. 2, 1995, now Pat. No. 6,110,708.

(30) Foreign Application Priority Data

Aug. 17, 1995 (JP) .............................................. 7-209698

(51) Int. Cl.[7] .............................. C12Q 1/70; C12N 7/00; C12N 5/00; C12N 5/06; C12N 5/02

(52) U.S. Cl. ......................... 435/5; 435/7.2; 435/235.1; 435/325; 435/339; 435/383

(58) Field of Search ......................... 530/350; 435/69.1, 435/7.1, 7.2, 471, 325, 5, 70.1, 71.1, 71.2, 235.1, 339, 383; 536/23.5

(56) References Cited

U.S. PATENT DOCUMENTS 6,110,708 A  8/2000  Wakamiya

FOREIGN PATENT DOCUMENTS

| WO | WO 91/07189 | 5/1991 |
| WO | WO 95/16697 | 6/1995 |

OTHER PUBLICATIONS

Taylor ME, et al. Structure and evolutionary originof the gene encoding a human serum amnnose–binding protein. Biochem J. vol. 262, pp. 763–771, 1989.*
Eda S, et al. Expression of recombinant conglutinin in *E. coli*. Seikagaku. vol. 67, p. 732, 1995.*
Malhotra R, et al. Binding of human collectins (SP–A and MBP) to influenza virus. Biochem. J. vol. 304, pp. 455–461, 1994.*
Anders, E.M. et al., "Bovine and Mouse Serum β Inhibitors of Influenza A Viruses Are Mannose–Binding Lectins," *Proc. Natl. Acad. Sci. USA*, 87(12):4485–4489 (Jun., 1990).

Eda, S. et al., Report No. 2002, "Expression of Recombinant Conglutinin in *E. Coli*, " *Seikagaku*, 67(7):732 Jul., 1995) (Japanese Wight English Translation).
Hartley, C.A. et al., "Two Distinct Serum Mannose–Binding Lectins Function as β Inhibitors of Influenza Virus; Identification of Bovine Serum β Inhibitor as Conglutinin," *J. Virology*, 66(7):4358–4363 (Jul., 1992).
Hoppe, H–J et al., "A Parallel Three Stranded α–helical Bundle at the Nucleation Site of Collagen Triple–Helix Formation," *FEBS Letters*, 344:191–195 (1994).
Kawasaki, N. et al., "Differentiation of Conglutination Activity and Sugar–Binding Activity of Conglutinin After Removal of $NH_2$–Terminal 54 Amino Acid Residues by Endogenous Serine Protease(s)," *Archives of Biochemistry and Biophysics*, 305(2):533–540 (Sep., 1993).
Kawasaki, N. et al., "Gene Organization and 5–40–Flanking Region Sequence of Conglutinin: A C–Type Mammalian Lectin Containing A Collagen–Like Domain," *Biochemical Biophyscial Research Communications*, 198(2):597–604 (Jan. 28, 1994).
Lee, Y–M et al., "Primary Structure of Bovine Conglutinin, a Member of the C–type Animal Lectin Family," *J. Biological Chemistry*, 266(5):2715–2723 (Feb. 15, 1991).
Lim, B–L et al., "Expression of the Carbohydrate Recognition Domain of Bovine Conglutinin and Demostration of Its Binding to iC3b and Yeast Mannan," *Biochemical Biophysical Research Communications*, 218(1):260–266 (1996).
Liou, L.S. et al., "Bovine Conglutinin (BC) mRNA Expressed in Liver: Cloning and Characterization of the BC cDNA Reveals Strong Homology to Surfactant Protein–D," *Gene*, 141(2):277–281 (1994).
Lu, J. et al., "Purification, Characteriztion and cDNA Cloning of Human Lung Surfactant Protein D," *Biochem. J.*, 284:795–802 (1992).
Malhotra, R. et al., "Binding of Human Collectins (SP–A and MBP) to Influenza Virus," *Biochem. J.*, 304(2);455–461 (1994).

(List continued on next page.)

Primary Examiner—Gary L. Kunz
Assistant Examiner—Robert S. Landsman
(74) Attorney, Agent, or Firm—Marshall, Gerstein & Borun

(57) ABSTRACT

A recombinant conglutinin which contains a collagen region consisting of six amino acids containing two amino acid sequences Gly-Xaa-Xaa (SEQ ID NO:3, wherein Xaa stands for a protein-constituting amino acid), the neck region of natural conglutinin and the sugar chain recognition region of natural conglutinin, has an antiviral activity (virus neutralizing activity), and is expected to be applicable to drugs; and a process for detecting anti-influenza A virus activity of a mannose-binding protein (MBP) or a human mannose-binding protein (hMBP) involving the step of treating influenza A virus-infected cells with the MBP or hMBP and measuring the level of the suppression of the budding of the virus in the virus-infected cells. An MBP and an hMBP having an anti-influenza A virus activity are disclosed.

12 Claims, 15 Drawing Sheets

OTHER PUBLICATIONS

Malhotra, R. et al., "Interaction of C1q Receptor With Lung Surfactant Protein A," *Eur. J. Immunol.,* 22:1437–1445 (1992).

Nikkei Biotechnology, Article No. 4, p. 9 "Stable Expression of Recombinant Bkg Had Been Succeeded and Viral Inhibition Activities Had Also Been Confirmed," (Sep. 25, 1995) (Japanese With English Translation).

Okuno, Y. et al., "Rapid Focus Reduction Neutralization Test of Influenza A and B Viruses in Microtiter System," *J. Clinical Microbiology,* 28(6):1308–1313 (Jun. 1990).

Reading, P.C. et al., "A Serum Mannose–Binding Lectin Mediates Complement–Deopendent Lysis of Influenza Virus–Infected Cells," *Biochemical and Biophysical Reasearch Communications,* 217(3):1128–1136 (Dec. 26, 1965).

Reading, P.C. et al., "A Serum Mannose–Binding Lectin Mediates Complement–Depedent Lysis of Influenza Virus–Infected Cells," *J. Leukocyte Biology,* 0(suppl.): 45 (1993) (Abstract No. 72).

Sheriff, S. et al., "Human Mannose–Binding Protein Carbohydrate Recognition Domain Treimerizes Through a Triple α–helical Coiled–Coil.," *Structural Biology,* 1(11):789–794 (Nov., 1994).

Strang, C.J. et al., "Ulstrastructure and Composition of Bovine Conglutinin," *Biochem. J.,* 234:381–389 (1986).

Sumiya, M. et al., "Molecular Basis of Opsonic Defect in Immunodeficient Children," *Lancet,* 337:15469–1570 (Jun. 29, 1991).

Super, M. et al., "Association of Low Levels of Mannan-Binding Protein Wigh a Common Defect of Opsonisation," *Lancet,* 2(8674):1236–1239 (Nov. 25, 1989).

Suzuki, Y. et al., "Cloning and Sequencing of a cDNA Coding for Bovine Conglutinin," *Biochemical Biophysical Research Communications,* 191(2):335–342 (Mar. 15, 1993).

Wakamiya, N. et al., "Isolation and Characterization of Conglutinin as an Influenza A Virus Inhibitor," *Biochemical Biophysical Research Communications,* 187(3):1270–1278 (Sep. 30, 1992).

Wakamiya et al., "The Mannose Binding Protein and Conglutinin in Bovine Serum Have a Antiviral Activity Against Influenza Virus," *Glycoconjugate J.,* 8:235 (1991) (No. 12.27).

Wakamiya, N. et al., Report No. 1P1–16, "Preparation of Recombinant Animal Serum Lectin and Its Role on Early Defense Against Viral Infection," *Proc. of the Genl. Mtg. of the Japanese S. for Immun,* 25:113 (Oct. 28, 1995) (Japanese With English Translation).

Wang, J–Y et al., "A Recombinant Polypeptide, Composed of the α–helical Neck Region and the Carbohydrate Recognition Domain of Conglutinin, Self–Associates to Give a Functionally Intact Homotrimer," *FEBS Letters,* 376:6–10 (1995).

* cited by examiner rBKg-CRD (µg/ml)

Fig. 10A rBKg-CRD (µg/ml)

Fig. 10B

```
                        SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 351 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

Ala Glu Met Thr Thr Phe Ser Gln Lys Ile Leu Ala Asn Ala Cys Thr
1               5                   10                  15

Leu Val Met Cys Ser Pro Leu Glu Ser Gly Leu Pro Gly His Asp Gly
            20                  25                  30

Gln Asp Gly Arg Glu Cys Pro His Gly Glu Lys Gly Asp Pro Gly Ser
        35                  40                  45

Pro Gly Pro Ala Gly Arg Ala Gly Arg Pro Gly Trp Val Gly Pro Ile
    50                  55                  60

Gly Pro Lys Gly Asp Asn Gly Phe Val Gly Glu Pro Gly Pro Lys Gly
65                  70                  75                  80

Asp Thr Gly Pro Arg Gly Pro Pro Gly Met Pro Gly Pro Ala Gly Arg
                85                  90                  95

Glu Gly Pro Ser Gly Lys Gln Gly Ser Met Gly Pro Pro Gly Thr Pro
            100                 105                 110

Gly Pro Lys Gly Glu Thr Gly Pro Lys Gly Gly Val Gly Ala Pro Gly
        115                 120                 125

Ile Gln Gly Phe Pro Gly Pro Ser Gly Leu Lys Gly Glu Lys Gly Ala
    130                 135                 140

Pro Gly Glu Thr Gly Ala Pro Gly Arg Ala Gly Val Thr Gly Pro Ser
145                 150                 155                 160

Gly Ala Ile Gly Pro Gln Gly Pro Ser Gly Ala Arg Gly Pro Pro Gly
                165                 170                 175

Leu Lys Gly Asp Arg Gly Asp Pro Gly Glu Thr Gly Ala Ser Gly Glu
            180                 185                 190
```

```
Ser Gly Leu Ala Glu Val Asn Ala Leu Lys Gln Arg Val Thr Ile Leu
        195                 200                 205

Asp Gly His Leu Arg Arg Phe Gln Asn Ala Phe Ser Gln Tyr Lys Lys
        210                 215                 220

Ala Val Leu Phe Pro Asp Gly Gln Ala Val Gly Glu Lys Ile Phe Lys
225                 230                 235                 240

Thr Ala Gly Ala Val Lys Ser Tyr Ser Asp Ala Glu Gln Leu Cys Arg
                245                 250                 255

Glu Ala Lys Gly Gln Leu Ala Ser Pro Arg Ser Ser Ala Glu Asn Glu
                260                 265                 270

Ala Val Thr Gln Met Val Arg Ala Gln Glu Lys Asn Ala Tyr Leu Ser
                275                 280                 285

Met Asn Asp Ile Ser Thr Glu Gly Arg Phe Thr Tyr Pro Thr Gly Glu
        290                 295                 300

Ile Leu Val Tyr Ser Asn Trp Ala Asp Gly Glu Pro Asn Asn Ser Asp
305                 310                 315                 320

Glu Gly Gln Pro Glu Asn Cys Val Glu Ile Phe Pro Asp Gly Lys Trp
                325                 330                 335

Asn Asp Val Pro Cys Ser Lys Gln Leu Leu Val Ile Cys Glu Phe
                340                 345                 350

(2) INFORMATION FOR SEQ ID NO:2:

(i) SEQUENCE CHARACTERISTICS:
        (A) LENGTH: 171 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

Gly Leu Pro Gly His Asp Gly Gln Asp Gly Arg Glu Cys Pro His Gly
1               5                   10                  15

Glu Lys Gly Asp Pro Gly Ser Pro Gly Pro Ala Gly Arg Ala Gly Arg
                20                  25                  30

Pro Gly Trp Val Gly Pro Ile Gly Pro Lys Gly Asp Asn Gly Phe Val
            35                  40                  45

Gly Glu Pro Gly Pro Lys Gly Asp Thr Gly Pro Arg Gly Pro Pro Gly
    50                  55                  60

Met Pro Gly Pro Ala Gly Arg Glu Gly Pro Ser Gly Lys Gln Gly Ser
65                  70                  75                  80

Met Gly Pro Pro Gly Thr Pro Gly Pro Lys Gly Glu Thr Gly Pro Lys
                85                  90                  95

Gly Gly Val Gly Ala Pro Gly Ile Gln Gly Phe Pro Gly Pro Ser Gly
                100                 105                 110

Leu Lys Gly Glu Lys Gly Ala Pro Gly Glu Thr Gly Ala Pro Gly Arg
        115                 120                 125

Ala Gly Val Thr Gly Pro Ser Gly Ala Ile Gly Pro Gln Gly Pro Ser
        130                 135                 140

Gly Ala Arg Gly Pro Pro Gly Leu Lys Gly Asp Arg Gly Asp Pro Gly
145                 150                 155                 160

Glu Thr Gly Ala Ser Gly Glu Ser Gly Leu Ala
                165                 170

(2) INFORMATION FOR SEQ ID NO:3:
```

```
    (i) SEQUENCE CHARACTERISTICS:
        (A) LENGTH: 3 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: misc.
        (B) LOCATION: 2
        (D) OTHER INFORMATION: /note= "2ND amino acid is a
            protein-constituting amino acid."

(ix) FEATURE:
        (A) NAME/KEY: misc.
        (B) LOCATION: 3
        (D) OTHER INFORMATION: /note= "3RD amino acid is a
            protein-constituting amio acid."

(xi) SEQUENCE DESCRIPTION: SEQ ID NO:3:

Gly Xaa Xaa
1

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthesized DNA"

(xi) SEQUENCE DESCRIPTION: SEQ ID NO:4:

GGCTCGAGGG GGAGAGTGGG CTTGCAGA                                              28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthesized DNA"

(xi) SEQUENCE DESCRIPTION: SEQ ID NO:5:

GGGAATTCTC AAAACTCGCA GATCACAA                                              28
```

METHODS FOR DETECTING ANTI-VIRAL ACTIVITY OF CALCIUM-DEPENDENT LECTINS

This application is a CIP of Ser. No. 09/011,375 filed May 22, 1998 now U.S. Pat. No. 6,110,708, which is a 371 of PCT/JP95/02035 filed Oct. 2, 1995.

TECHNICAL FIELD

The present invention relates to recombinant conglutinin having anti-virus activities (neutralization activities) which are expected to be applied to medicines and producing method thereof, and a method for detecting physiological activities of collecting.

BACKGROUND ART

Conglutinin is an animal lectin belonged to calcium-dependent mammalian C-type lectin family and existed in the bovine serum. Whole amino acids sequence (SEQ ID No.: 1) had been analyzed by Lee et al., [Lee et al., *J Biol. Chem.*, Vol. 266, pp. 2715–2723, 1991].

C-type lectin comprises basic unit having the four unique regions of (1) N-terminal region contained much cysteine, (2) collagen-like region, (3) neck region and (4) carbohydrate recognition domain (CRD) [Malhortra et al., *European Journal Immunology*, Vol. 22, pp. 1437–1445, 1992].

Besides conglutinin, C-type lectin includes Mannan-Binding Proteins (MBP), Surfactant Protein A (SP-A) and Surfactant Protein D (SP-D), and they are generally called as collectin.

In vertebrates, mechanisms involving specific antibody reaction and immune response through the cells are considered as a main host-defense system against inversion of the pathogenic bacteria. However, recently, non-specific immune response by these lectins seems that it may play an important role to neutralize and remove the various microorganisms in the puerile subjects having the maternal transmigration antibody and the undeveloped specific defense system [Super et al., *Lancet*, Vol.II, pp. 1236–1239, 1989].

Regarding the role of these lectins on biological defense in host organism, it is reported that infection will be easily spread by, for example, the reduction of the mannan-binding protein concentration in blood due to genetic mutation of the mannan-binding protein [Sumiya et al., *Lancet*, Vol. 337, pp. 1569–1570, 1991].

The present inventor once reported that the conglutinin and the mannan-binding protein inhibit infection and hemagglutination inhibition activity of H1 and H3 Type Influenza A Viruses (Wakamiya et al., *Glycoconjugate J.*, Vol. 8, p. 235, 1991; Wakamiya et al., *Biochem. Biophys. Res. Comm.*, Vol. 187, pp. 1270–1278, 1992).

Thereafter, the research group of the present inventor isolated cDNA clone encoding the conglutinin and found that there is the closer correlation between gene of the conglutinin and that from the various surfactant protein-D [Suzuki et al., *Biochem. Biophys. Res. Comm.*, Vol. 191, pp. 335–342, 1993].

Accordingly, the conglutinin have been expected as useful material for physiologically active medicine component, but amount of the conglutinin to be obtained from the bovine serum is less. Further, continuous production of the conglutinin is quite difficult because source thereof is completely depended on an animal body. Expression of the conglutinin in *Escherichia coli* by the genetic recombinant techniques had been tried to realize the large scale production of the conglutinin.

In such process, first of all, whole cDNA of the conglutinin was amplified by PCR (Polymerase Chain Reaction) method, then the amplified genes were introduced into the expression vector pRSET-A and were expressed with M13/T7 phage. The recombinant conglutinin obtained was analyzed. Although expression of the recombinant conglutinin had been confirmed, expressed amounts are less to be barely detected by Western blotting. This approach is inconvenient to the large-scale production of the conglutinin.

Similar methods had also been tried by using another expression vectors, but the same or less expression level had merely detected by any of the vectors. Anyway, an effective expression system have not yet been realized in the art. This seems due to difficulties in expressing the conglutinin because *Escherichia coli* does not possess proteins of the structure like collagen-like region. Further, yield of the conglutinin produced from an eukaryotic cells is little, and some of the conglutinin may sometimes have an inappropriate post-transcriptional modification.

As stated above, although the conglutinin have been expected as an useful medicine component, neither the natural source nor the genetic recombinant techniques could provide the large amount of the conglutinin.

DISCLOSURE OF INVENTION

The present inventions are established to solve the aforenoted problems in the prior art, and they are based on the findings that large amount of the present recombinant conglutinin can be produced according to the previously noted expression system, wherein the recombinant conglutinin comprises (i) a part of the collagen region of the conglutinin consisting of 171 amino acids sequence (SEQ ID No.: 2), namely, an extremely short collagen region consisting of six amino acids comprising two units of amino acids sequence of Gly-Xaa-Xaa (SEQ ID No.: 3; $2^{nd}$ and $3^{rd}$ amino acids are protein-constituting amino acid), (ii) the neck region and (iii) the carbohydrate recognition domain.

Despite that the recombinant conglutinin of the present invention comprises the extremely short collagen region, the neck region and the carbohydrate recognition domain, they maintain the similar activities to be expressed by the native conglutinin including the activities of the sugar binding specificities, conglutination activities depending on calcium, hemagglutination inhibition (HI) activities against Influenza A viruses, neutralization activities and viral growth (infection spread) inhibition activities.

Further, the method for detecting the physiological activities of the collectins can be used to detect the physiological activities of the collectins including the conglutinin by evaluating inhibition effects on budding of the viruses from the cells preinfected with viruses, in particular, with influenza A virus. According to this method, physiological activities of the collectins can exactly be detected even if they were once determined as inactive by the conventional detection method (e.g., detection by neutralization activities), physiological activities of the collectins would therefore be appropriately evaluated from different aspects. Further, the present detection method may provide a landmark to determine a preferable use of the collecting.

BRIEF DESCRIPTION OF DRAWINGS

FIGS. 10A and 10B show viral growth (infection spread) inhibition activities on the recombinant conglutinin (rBKg-CRD);

BEST MODE FOR CARRYING OUT THE INVENTION

The recombinant conglutinin of the present inventions will be explained in detail along with the following Examples, but, as a matter of course, scope of the present inventions should not be limited based on the disclosures of the Examples.

Examples are consisting of, expression of conglutinin fragments in *Escherichia coli* (Example 1), structural analysis on the recombinant conglutinin (Example 2), evaluation on sugar binding activities of the recombinant conglutinin and the native conglutinin (Example 3), evaluation on conglutination activities of the recombinant conglutinin (Example 4), activities on hemagglutination inhibition (HI) (Example 5), neutralization activities (Example 6), activities on viral growth (infection spread) inhibition (Example 7), and detection of physiological activities by collectins (Example 8).

EXAMPLE 1

Expression of Conglutinin Fragments in *Escherichia coli*

(1) Preparation of Conglutinin DNA Fragments with RT-PCR

In accordance with the method by Suzuki et al., (*Biochem. Biophys. Res. Comm.*, Vol. 191, pp. 335–342, 1993), primers for PCR containing the following sequences were designed based on cDNA of the bovine conglutinin and were synthesized. Each of these primers has cleavage sites of the restriction enzymes XhoI and EcoRI.

5'-GGCTCGAGGGGGAGAGTGGGCTTGCAGA-3' (SEQ ID No.: 4)
5'-GGGAATTCTCAAAACTCGCAGATCACAA-3' (SEQ ID No.: 5) 50 μl of reaction mixture was used as a sample containing 1 X buffer, 1 μM primers, 200 μM dNTPs, 1 U Deep Bent DNA polymerasae (New England Biolabs) and 10 ng cDNA. Using PCR reactor of Atto (Zymoreactor (Registered Trademark)), PCR was performed for 35 cycles, each cycle of which consists of denaturation at 92° C. for one minute, annealing at 60° C. for one minute and elongation at 72° C. for two minutes. PCR products of 497 bp was produced.

(2) Preparation of Transformants by Conglutinin Fragments

Figure 1:
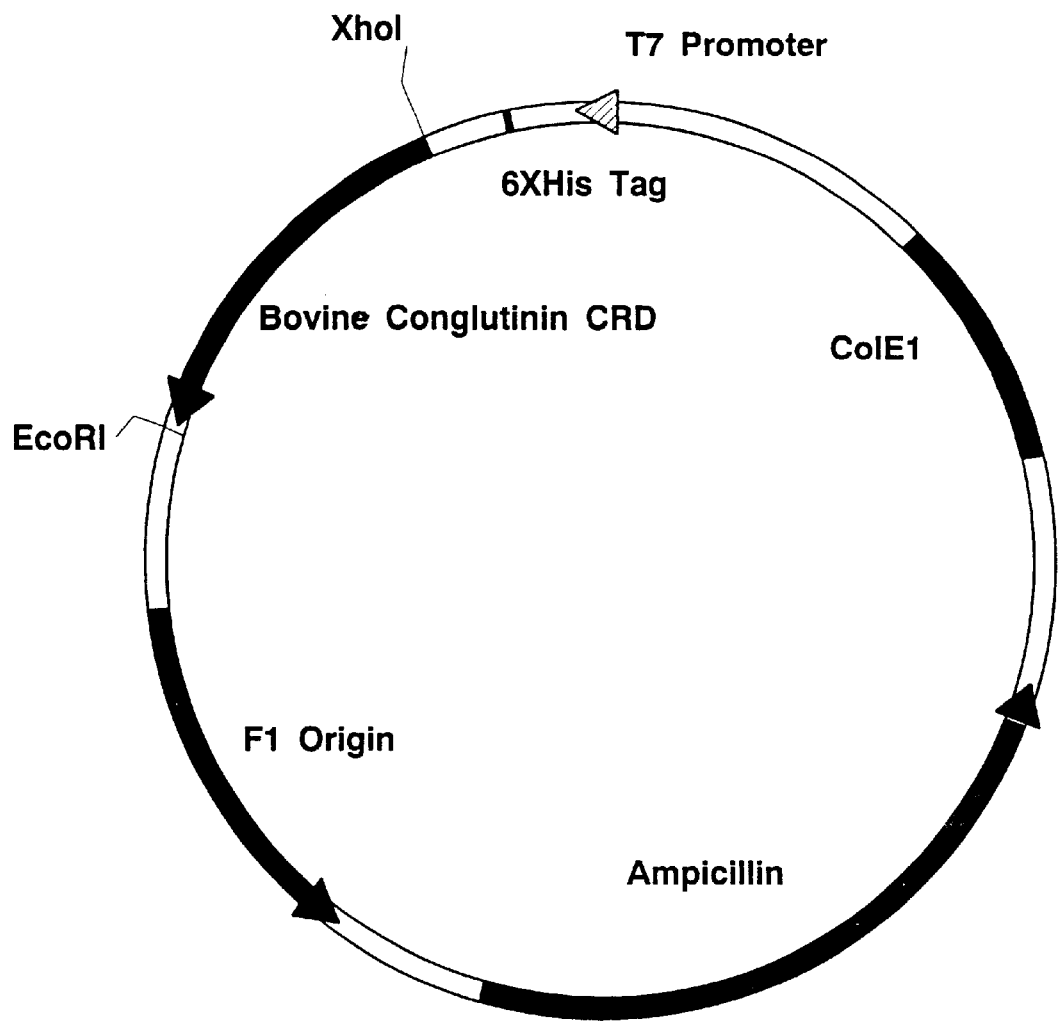
FIG. 1 shows a vector to transform subjects with the recombinant conglutinin DNA.

PCR products of Example 1(1) were digested with the restriction enzymes xhoI and EcoRi, then were inserted into the expression vector pRSET-A (Invitrogen) with DNA ligation kit (Takara Shuzo). Then, pRSET vector so prepared from pRSET-A containing bovine conglutinin cDNA fragment was transfected into *Escherichia coli* JM109 and transtormants obtained that have the conglutinin DNA fragments corresponding to 631 bp through 1113 bp of the native conglutinin DNA (FIG. 1).

Sequences of these fragments were corresponding to $19^{st}$ through $351^{st}$ amino acids of native conglutinin, namely, PCR exactly amplified the sequences having the short collagen region, the neck region and the carbohydrate recognition domain. Further, there was no error in the PCR reaction. Accordingly, desirable stable transformants were obtained which can remarkably produce such conglutinin DNA fragments.

(3) Expression and Purification of Recombinant Conglutinin Proteins

Transformed single colony containing whole insert (conglutinin DNA fragment) was incubated overnight at 37° C. on SOB medium (containing 50 μg/l ampicillin). 1.2 ml of culture solution was inoculated onto 200 ml SOB medium (containing 50 μg/l ampicillin) and cells were allowed to grow to be approximately 0.3 of $OD_{600nm}$. Isopropyl-1-thio-β-D-galactoside (IPTG) was then added to become final concentration of 1 mM and the culture was grown for additional one hour. The cells were infected at MOI 5 pfu/cell with M13 phage containing T7 ΔRNA polymerase gene driven by the *Escherichia coli* lactose promoter and incubated for another three hours. Bacteria was collected by centrifugating the culture solution at 3,000 g for 15 minutes.

Pellets of bacteria were suspended in 20 ml Buffer A (guanidine chloride 6 M, sodium phosphate 20 mM, sodium chloride 500 mM, pH 7.8) and were lysed with sonication (15 seconds, power 70%, 10 times). After centrifugation at 43,000 g for 30 minutes, Nickel-NTA agarose (Qiagen) was added to the supernatant and they were left for 15 minutes.

Products were poured into a column. The column was washed with TBS/NT solution (Tris-HCl 20 mM, sodium chloride 140 mM, 0.05% sodium azide, 0.05% Tween 20 (Registered Trademark), pH 7.4) and further with TBS/NTC solution (TBS/NT solution containing 5 mM calcium chloride). Fusion proteins were eluted with TBS/NTC solution containing 0.5 mM imidazole. Eluted solution was dialyzed three times against 1,000 times volume of TBS/NTC solution. After dialysis and centrifugation of the samples, the supernatant was poured into the Mannan-Sepharose Column (Affinity Column prepared by binding Mannan (Sigma) to CNBr activated Sepharose 4B (Pharmacia)). After washing with the TBS/NTC solution, proteins in the column were eluted with TBS/NTC solution containing 5 mM N-acetylglucosamine. Purity of the recombinant conglutinin produced was determined by SDS-PAGE or Western blotting as noted later.

(4) SDS-PAGE

Figure 2:
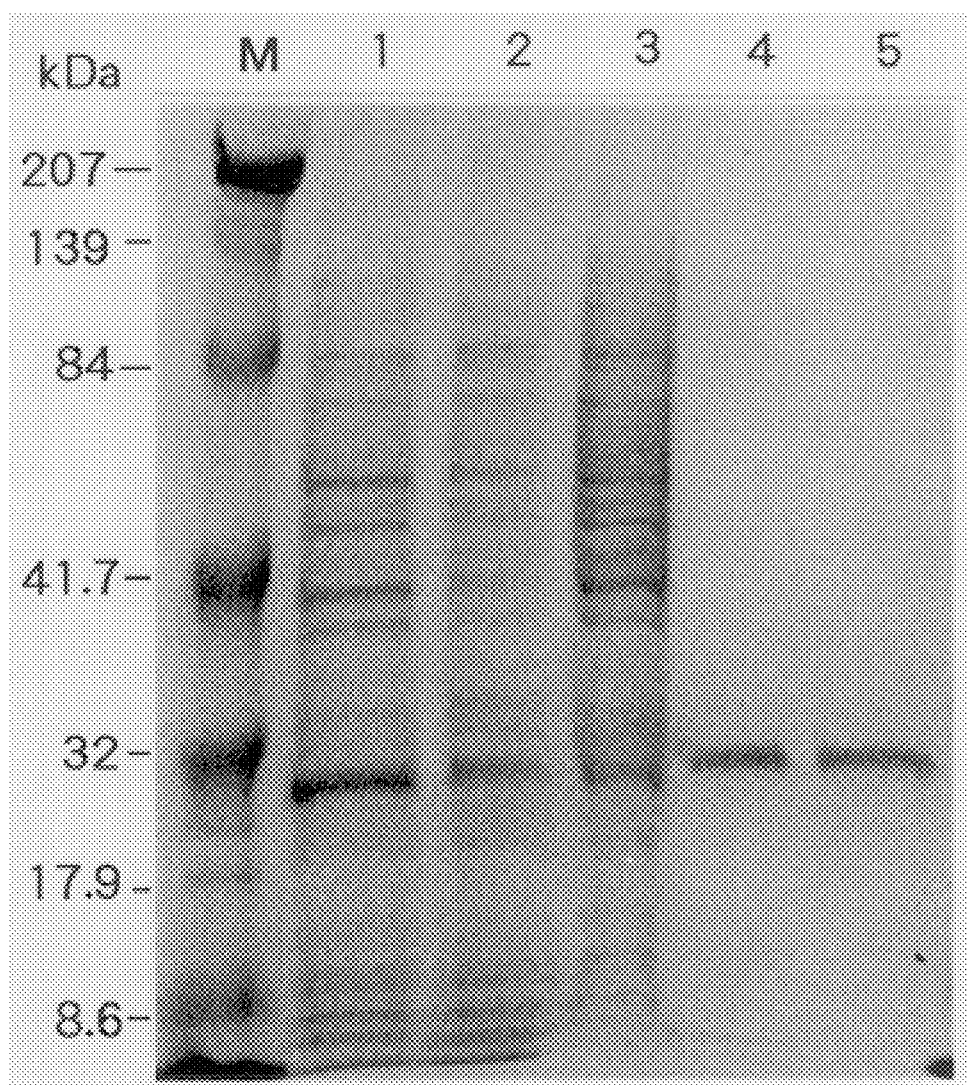
FIG. 2 shows a result of SDS-PAGE on the recombinant fusion conglutinin.

In SDS-PAGE, polyacrylamide gel having the 4–20% concentration gradient was employed. Polypeptide was stained with 1% Coomassie Brilliant Blue (CBB). Results were shown in FIG. 2. In FIG. 2, Lane M is standard proteins, Lane 1 is a lysate of whole cell, Lane 2 is a soluble fraction by guanidine chloride, Lane 3 is an insoluble fraction by guanidine chloride, Lane 4 is an eluted fraction from nickel-agarose column and Lane 5 is an eluted fraction from Mannan-Sepharose column. Although the molecular weight of the recombinant fusion conglutinin deduced from the amino acids sequences was 22.5 kDa, the molecular weight analyzed by SDS-PAGE was 27 kDa. Despite the digestion of the recombinant conglutinin with an enterokinase was not well, N-terminal amino acids sequence in the digested minor recombinant conglutinin was coincided with that of the matured conglutinin.

(5) Mannan-Sephalose Affinity Chromatography, SDS-PAGE and Western Blotting on Each Fraction Eluted fractions from Mannan-Sephalose Column were analyzed by SDS-PAGE under the conditions of polyacrylamide gel having 4–20% concentration gradient and 1% Coomassie Brilliant Blue staining. Proteins were transferred to nitrocellulose membrane and were incubated with 2,000-fold diluted rabbit anti-conglutinin serum. Then, they were reacted with anti-rabbit IgG-conjugated biotin (Vector) and finally with alkaline phosphatase-conjugated streptavidin (BRL). NBT/BCIP (BRL) was used as substrate for the alkaline phosphatase.

Figure 3:
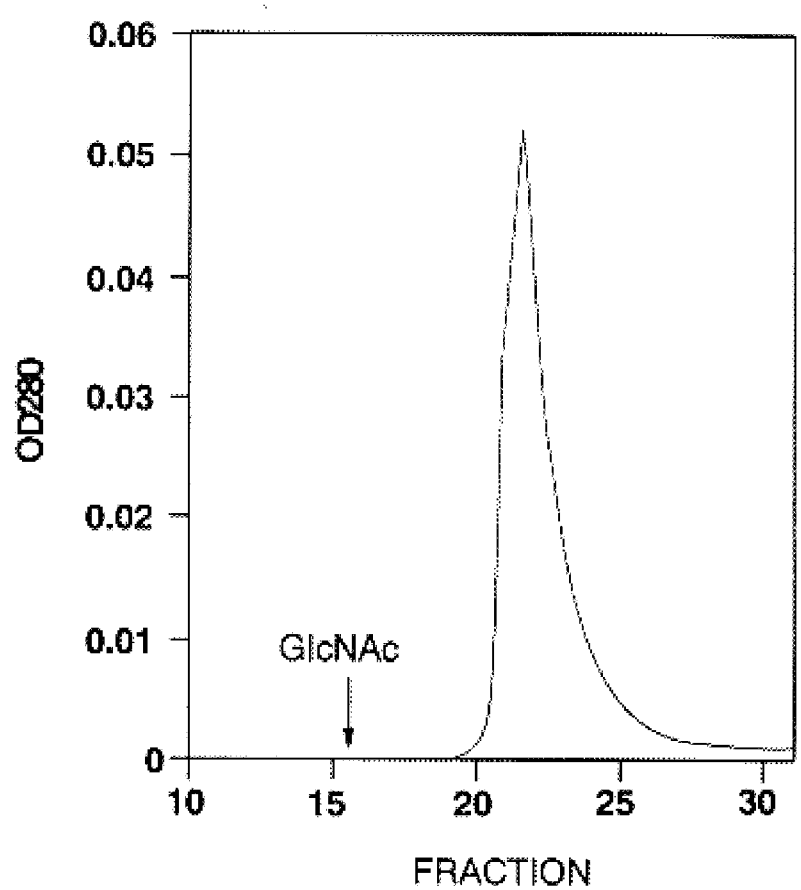
FIG. 3 shows a result of absorbance, CBB staining and Western blotting on each fraction by Mannan-Sepharose Affinity Chromatography.
Figure 3:
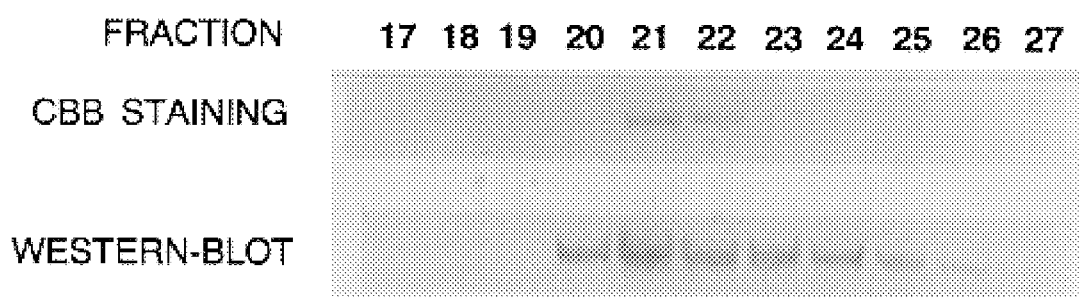

Elution pattern was shown in FIG. 3. Like the native conglutinin, the recombinant conglutinin had been eluted with 5 mM N-acetylglucosamine. This is to demonstrate that these fusion proteins have strong affinity against mannan. Final yield of the purified recombinant conglutinin was 2.8 mg per one liter of culture solution of *Escherichia coli*.

EXAMPLE 2

Structural Analysis of Recombinant Conglutinin (1) Crosslinking of Recombinant Fusion Conglutinin Native conglutinin consists of enneamer (9 mer) through octadecamer (18 mer) polypeptides (Kawasaki et al., *Arch. Biochem. Biophys.*, vol. 305, pp. 533–540, 1993). Molecular weight of the biggest polymer is approximately 1,000 kDa, and structure of the typical polymer forms four cross-shaped trimer (Strang et al., *Biochem. J*, Vol. 234, 381–389, 1986). Then, the structure of the recombinant conglutinin had also been analyzed.

Figure 4:
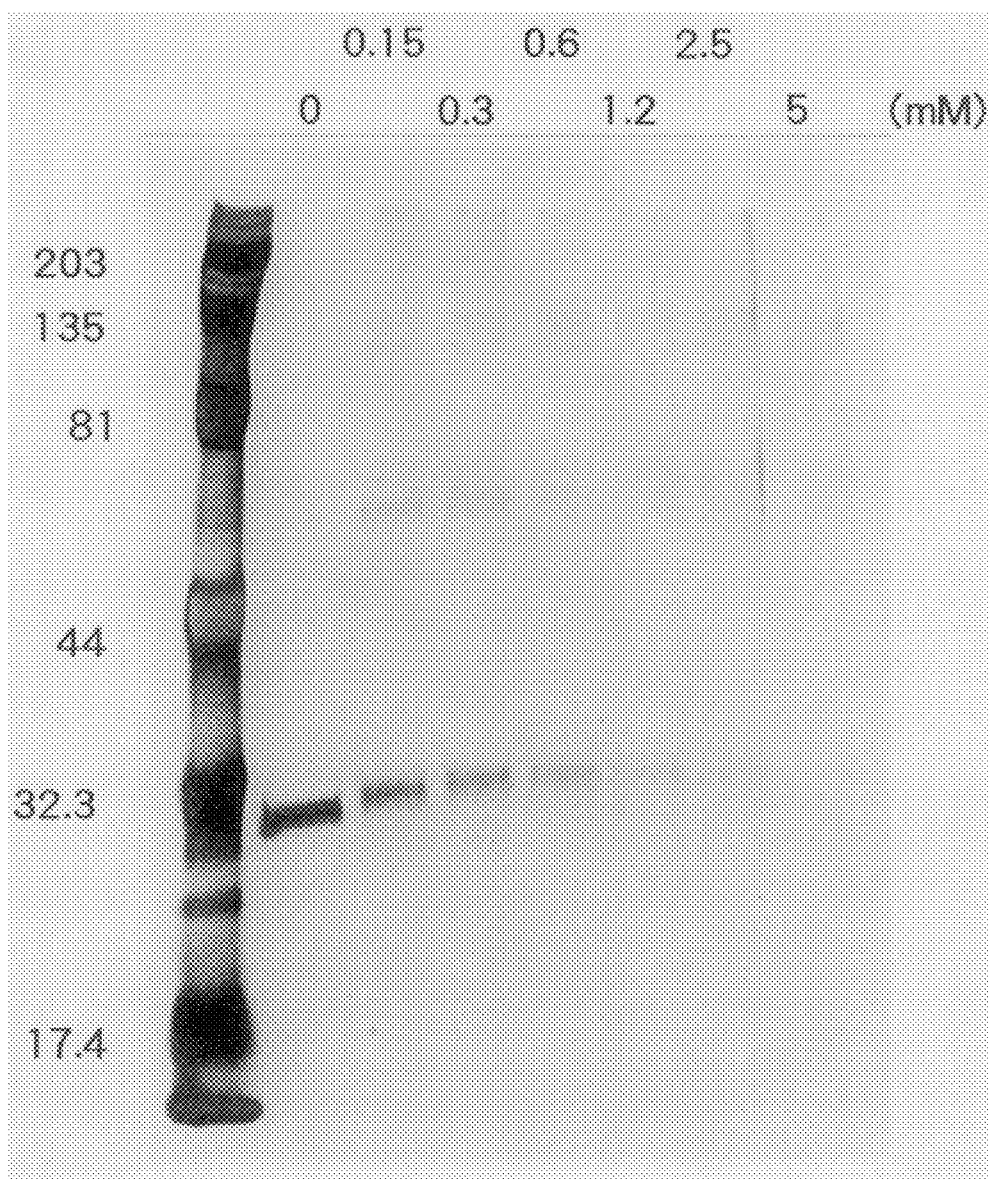
FIG. 4 shows a result of SDS-PAGE on the fractions treated with bis(sulfosuccinymidil)suberate.

The recombinant conglutinin proteins were dissolved with the PBS buffer containing 10 mM calcium chloride in the concentration of 22.8 μg/ml. Samples were treated at 37° C. for 20 minutes with 0 mM, 0.15 mM, 0.3 mM, 0.6 mM, 1.2 mM, 2.5 mM, and 5 mM bis(sulfosuccinymidil)suberate, and were analyzed with SDS-PAGE of 4–20% concentration gradient. Results were shown in FIG. 4. It was confirmed from the results of FIG. 4 that the recombinant fusion conglutinin consists of the monomer and the trimer having the molecular weight of 27 kDa.

(2) Gel Filtration Chromatography

Purified recombinant conglutinin was applied to Superose 6 (Pharmacia)at a flow rate of 0.5 ml/minute with TBS buffer containing 10 mM EDTA, pH 8.0. Then, 40 μg of the recombinant conglutinin was applied to this column. Fractions were monitored at 280 mn. Amount of the collected recombinant proteins were assayed with Coomassie Proteins Assay Reagent (Pierce).

Figure 5A:
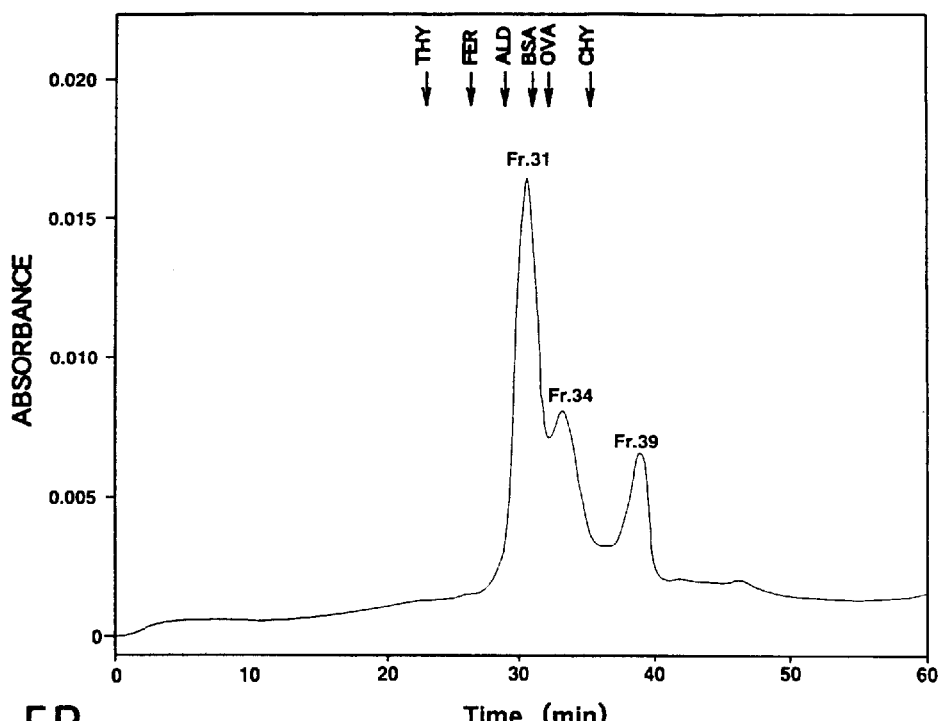
FIGS. 5A, 5B, and 5C show a result of gel filtration chromatography on the recombinant conglutinin.
Figure 5B:
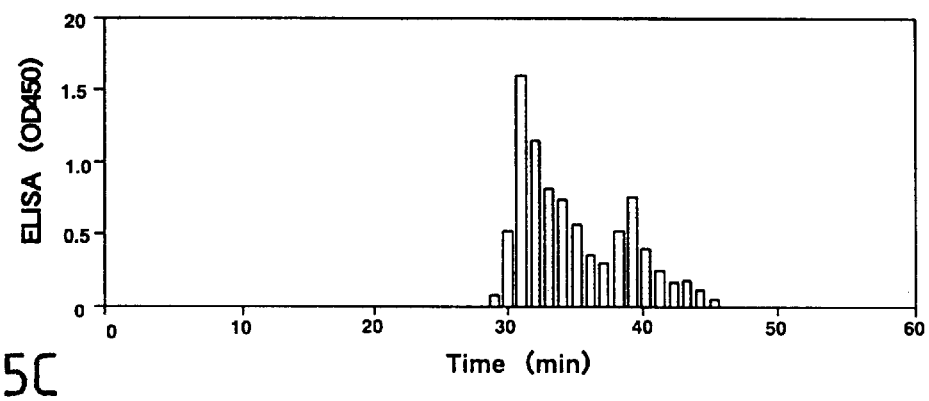
Figure 5C:
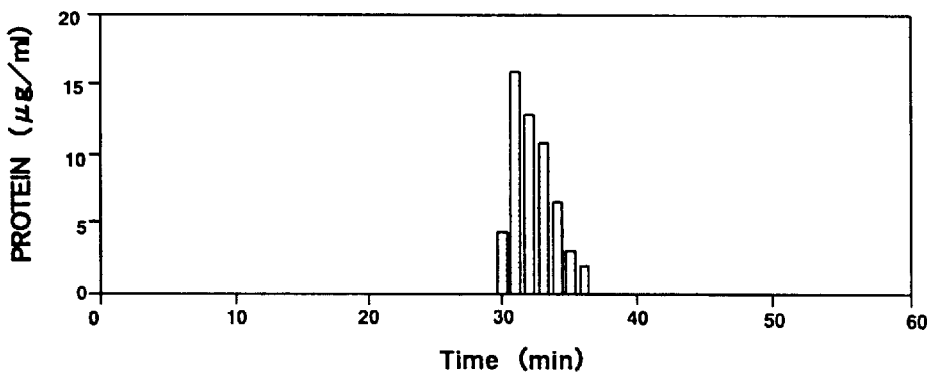

Each fraction was then applied to Sandwich ELISA System employing the following anti-bovine conglutinin rabbit serum. Standard Molecular Weight Kit of Pharmacia (thyroglobulin (THY), ferritin (FER), catalase, aldolase (ALD), albumin (BSA), ovalbumin (OVA), chymotrypsinogen A (CHY), ribonuclease A) was used to calibrate the column. As shown in FIG. 5, three major peaks of 94 kDa ($31^{st}$ fraction), 39 kDa ($34^{th}$ fraction) and 4.6 kDa ($39^{th}$ fraction) had been found. However, no protein was detected in the $39^{th}$ fraction by a quantitive analysis. Fraction of 4.6 kDa had not been stained in the silver staining of SDS gels. This fraction was identified as non-peptide by the ultraviolet absorbance at 200 nm and 280 nm.

Based on the above results, it is apparent that the conglutinin may form trimer without the collagen region. Further, these results correspond to the facts that, like the conglutinin, the recombinant human mannan-binding protein or bovine lung surfactant protein D respectively belonged to C-type lectin forms trimer through the neck region without the collagen region (Sheriff et al.,*Nature Struct. BioL*, Vol. 1, pp. 789–794, 1994; Hoppe et al., *FEBSLett.*, Vol. 344, pp. 191-195, 1994).

EXAMPLE 3

Sugar Binding Activities by Recombinant Conglutinin and Native Conglutinin (1) Sugar Binding Activities Microtiter Plates were coated with 100 μl coating buffer (15 mM sodium carbonate, 35 mM sodium hydrogencarbonate, 0.05% sodium azide, pH 9.6) containing yeast mannan (10 μg/ml) at 4° C. overnight. After each treatment step, the plates were washed three times with TBS/NTC solution (20 mM Tris-HCl, 140 mM sodium chloride, 0.05% sodium azide, 0.05% Tween 20 (Registered Trademark), pH 7.4, 5 mM calcium chloride). After completing the coating of the plates, the plates were treated and blocked with TBS/NTC solution containing 1% bovine serum albumin at room temperature for one hour.

Single dilution (0, 1, 10, 100 and 1,000 ng/ml) of the recombinant conglutinin or the native conglutinin, or mix dilution of the various sugars and such single dilution were added to TBS/NTC or TBS/NTC containing 20 mM N-acetyl-D-glucosamine (A) or 10 mM EDTA.

Rabbit anti-native conglutinin serum and goat anti-rabbit IgG horseradish peroxidase conjugates (Bio-Rad) respectively 1,000 or 2,000-fold diluted with TBS/NTCB were added thereto and they were incubated at 37° C. for one hour. Finally, 100 μl of TMB substrates (TMB Microwell Peroxidase Substrates System; KPL) was added to each well. Before or after the addition of 100 μl of IM phosphoric acid, absorbance at 450 or 655 nm was measured (TiterTech MultiScan Plus MKII Plate Reader; Flow Rubs). Then, evaluation on sugar inhibiting activities were performed according to the method of Lu et al., (*Biochem. J*, Vol. 284, pp. 795–802, 1992) employing this ELISA system.

Figure 6:
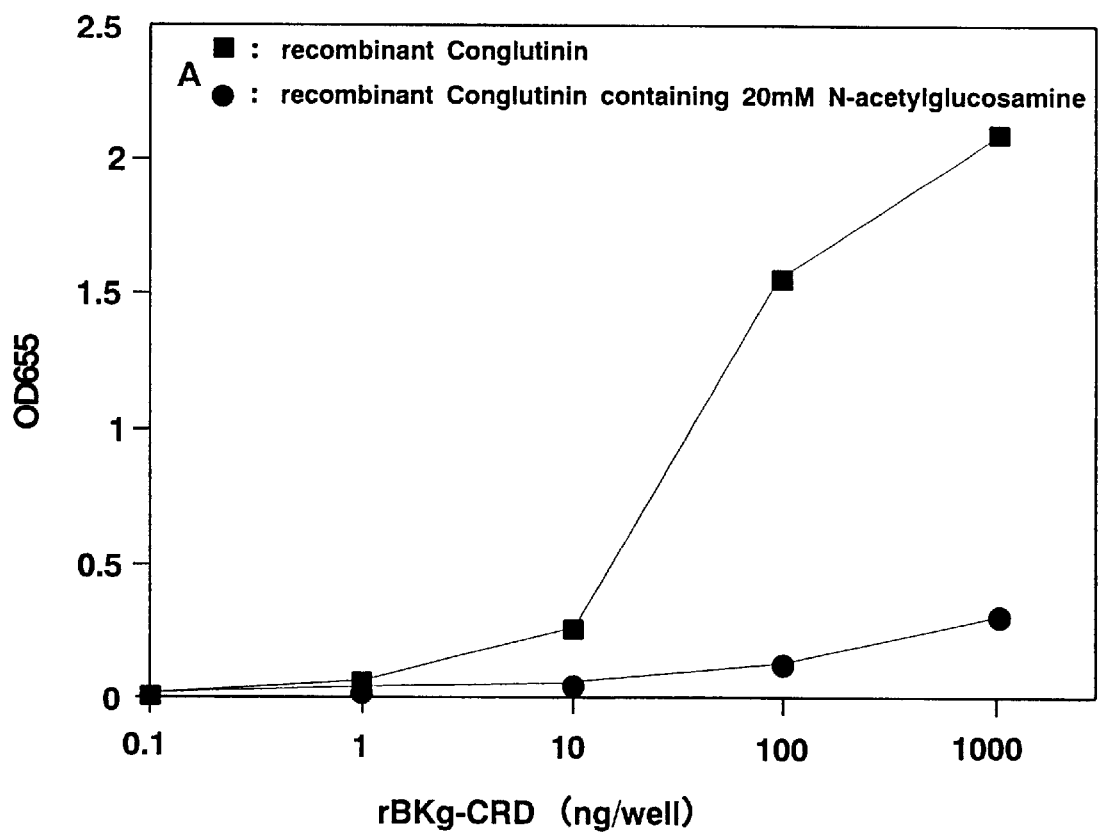
FIG. 6 is a graph showing binding-activity between mannan and the recombinant conglutinin or that containing 20 mM N-acetylglucosamine.
Figure 7:
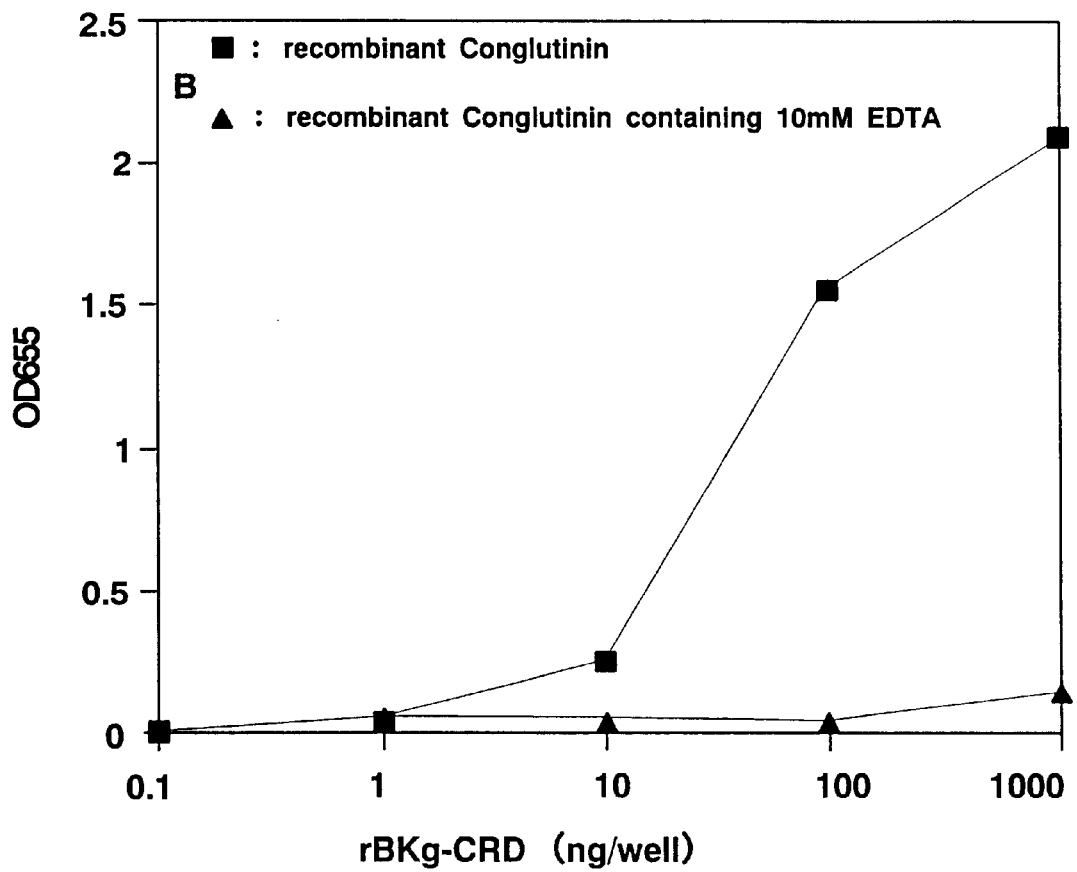
FIG. 7 is a graph showing binding-activity between mannan and the recombinant conglutinin or that containing 10 mM EDTA.

After coating the microtiter plates with yeast mannan (1 μg/well), the recombinant conglutinins were reacted with sugars. Sugar binding specificity ($I_{50}$) was shown as sugar concentration to halve binding activities. Results are shown in Table 1. Obviously from Table 1, sugar binding activities with the recombinant conglutinin are substantially same to that of the native conglutinin. Then, as shown in FIGS. 6 and 7, like the native conglutinin, binding activities of the recombinant conglutinin were dependent on calcium ion. Further, these binding activities were inhibited by N-acetylglucosamine. On the other hand, tags of histidine fused to the recombinant conglutinin were not involved in the binding activities to mannan and binding specificities.

TABLE 1

Sugar Binding Specificities on
Recombinant Conglutinin and Native Conglutinin

| | $I_{50}$ (mM)* | |
|---|---|---|
| | Recombinant Conglutinin | Native Conglutinin** |
| N-Acetyl-D-Glucosamine | 0.65 | 1.4 |
| Fucose | | 41.5 |
| L-Fucose | 37.8 | |
| D-Fucose | 55.3 | |
| D-Mannose | 12.3 | 19.5 |
| Maltose | 25.8 | 49.0 |
| N-Acetyl-D-Mannosamine | 26.6 | |
| Glucose | 39.5 | 41.5 |
| Galactose | 46.8 | >100 |
| N-Acetyl-D-Galactosamine | ∞*** | |
| Lactose | >100 | ∞*** |

*Sugar concentration to halve binding activity with mannan.
**Lu, J. et al., Biochem. J., vol. 284, pp. 795–802 (1992)
***Inhibition-activity was not detected.

EXAMPLE 4

Conglutination Activities by Recombinant Conglutinin

Conglutination activities or the recombinant conglutinin and the native conglutinin were evaluated by Microtiter plate assay system. Sheep erythrocyte cells with iC3b were prepared according to the method of Wakamiya et al., (*Biochem. Biophys. Res. Comm.*, Vol. 187, pp. 1270–1278, 1992). Namely, 1% sheep erythrocyte cells with iC3b were prepared by priming with a mixture of ten-fold diluted fresh horse serum and equivalent amount of anti-Forssmann antibody, and incubated at 37° C. for ten minutes.

Figure 8:
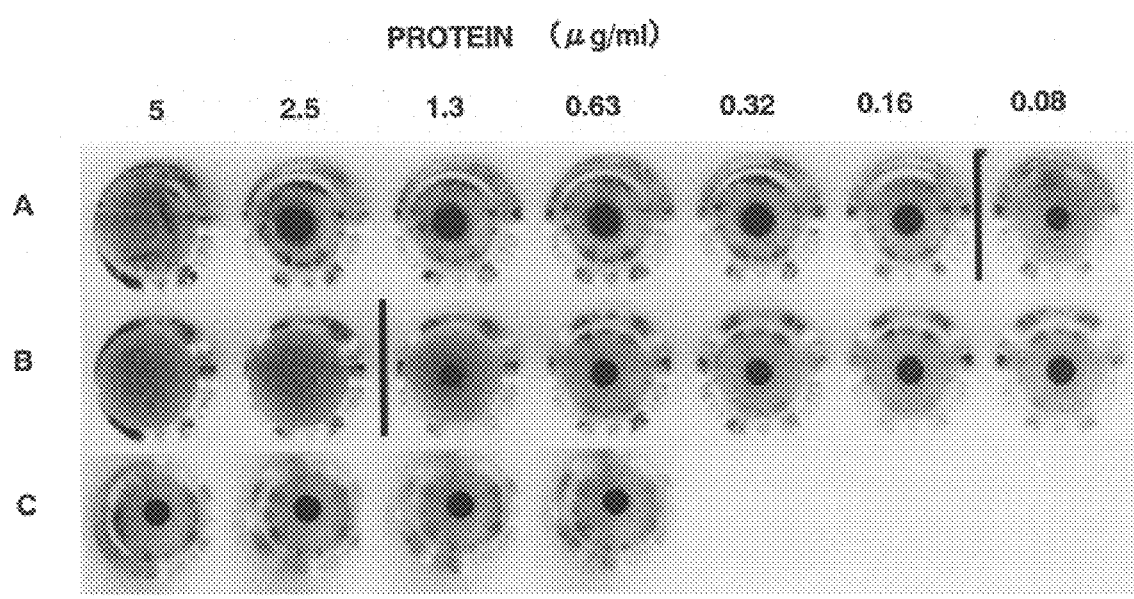
FIG. 8 shows conglutination activities on the recombinant conglutinin and the native conglutinin with microtitel plate assay system.

50 µl of 1% sheep erythrocyte cells with iC3b and 50 µl of the recombinant conglutinin or 50 µl of the native conglutinin were added to the raw veronal buffer or the veronal buffer containing 30 mM N-acetylglucosamine. Then, they were incubated at 37° C. and the conglutination activities thereon were detected. The lowest concentration of the proteins to cause agglutination is regarded as titer of conglutination, then the results are shown in FIG. 8. In FIG. 8, Lane A is the native conglutinin, Lane B is the recombinant conglutinin and Lane C is the recombinant conglutinin containing 30 mM N-acetylglucosamine. Titer of conglutination on the native conglutinin was 0.16 µg/ml, while that of the recombinant conglutinin was 1.3–2.5 µg/ml. Such activities were completely inhibited by 30 mM N-acetylglucosamine (GlcNAc).

EXAMPLE 5

Hemagglutination Inhibition (HI) Activities (1) Viruses

Influenza A virus, namely, Influenza A virus A/Ibaraki/1/90 (H3N2: Influenza A virus (A-Hong Kong)), A/Osaka1869/95 (H3N2), A/Beijing/352/89 (H3N2), A/Adachi/1/57 (H2N2) and A/Suita/1/89 (H1N1:Influenza A virus (A-U.S.S.R.)) were used to evaluate Hemagglutination Inhibition (HI) Activities. Viruses were proliferated with CAM (chorioallantoic membrane) according to the standard method and were stored at −70° C. until use. As a growth medium for the viruses, Eagle MEM medium containing 3% vitamin for tissue cultures, 0.2% albumin, 0.1% glucose and 0.2 ng/ml acetylated trypsine was used.

(2) Hemagglutination Inhibition (HI) Activities By Recombinant Conglutinin

Figure 9:
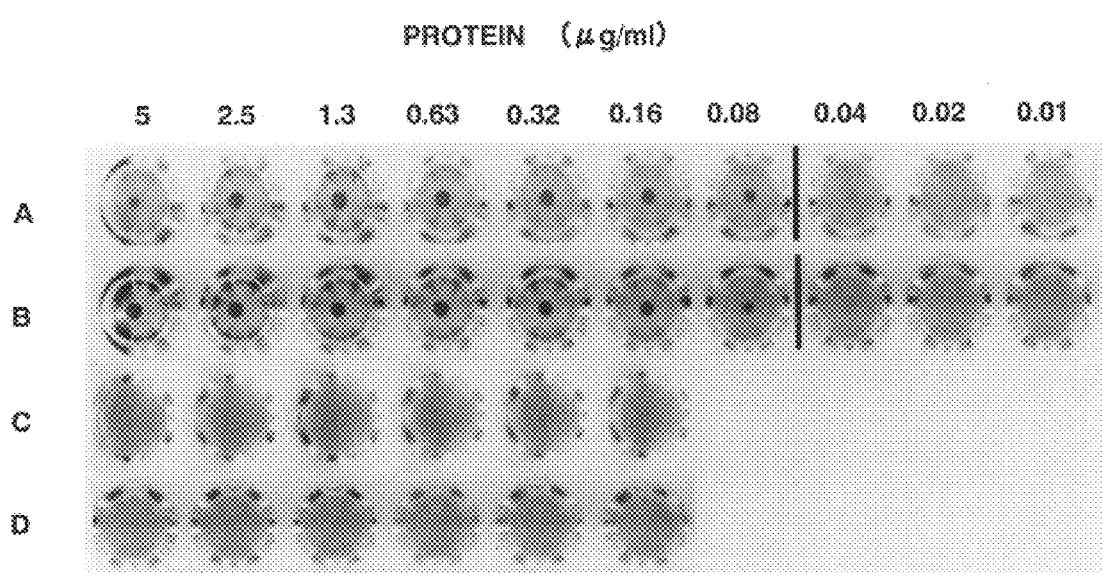
FIG. 9 shows hemagglutination inhibition (HI) activities on the native conglutinin and the recombinant conglutinin.

In accordance with the method of Okuno et al., (*J Clin. Microbiol.*, Vol. 28, pp. 1308–1313, 1990), experiments were performed in 96-well microtiter plates with 1% chick's erythrocytes. The ether-treated virus antigens from a hen egg antigen was used. No additive had been added to mixed cultivation solution of TBS/C (TBS solution containing 5 mM sodium chloride) except for 30 mM N-acetylglucosamine or 10 mM EDTA. After incubation at room temperature for one hour, effects on the recombinant conglutinin fragments (rBKg-CRD) against viral hemagglutination on chick's erythrocytes were observed. Results are shown in Table 2. Results on Influenza A virus A/Ibaraki/1/90 are shown in FIG. 9. In FIG. 9, Lane A is the native conglutinin, and Lanes B, C and D are directed to the recombinant conglutinin fragments, in which the Lane B is no additives, Lane C is added thereto 30 mM N-acetylglucosamine and Lane D is added threreto 10 mM EDTA.

TABLE 2

Expression Concentration (µg/ml) on Hemagglutination Inhibition (HI) by Recombinant Conglutinin and Native Conglutinin

| Virus | Recombinant Conglutinin | Native Conglutinin |
|---|---|---|
| A/Suita/1/89(H1N1) | 0.15–0.3 | 0.08 |
| A/Adachi/1/57(H2N2) | >5 | >5 |
| A/Ibaraki/1/90(H3N2) | 0.08–0.3 | 0.08 |
| A/Beijing/352/89(H3N2) | 0.3 | nt* |
| A/Osaka/869/95(H3N2) | 0.15 | nt* |

*Not tested.

Hemagglutination Inhibition (HI) activities were depended on dosages and calcium. Further, Hemagglutination Inhibition (HI) activities of the recombinant conglutinin are substantially the same level to the titer of the native conglutinin, rat surfactant protein D, human surfactant protein D (Hartshorn et al., *J Clin. Invest.*, Vol. 94, pp. 311–319, 1994).

EXAMPLE 6

Neutralization Activities (1) Viruses

Influenza A virus, namely, Influenza A virus A/Ibaraki/1/90 (H3N2:Influenza A virus (A-Hong Kong)) and A/Suita/1/89 (H1N1:Influenza A virus (A-U.S.S.R.)) were used.

(2) Neutralization Activities

Neutralization activities were evaluated according to the method of Okuno et al., (*J Clin. Microbiol.*, Vol. 28, pp. 1308–1313, 1990). Influenza viruses and the recombinant conglutinin were mixed on 96-well microtiter plate, and the mixtures were incubated for several days in Madin-Darby Canine Kidney (MDCK) cells grown in the Eagle MEM medium containing 10% fetal bovine serum. Then, the neutralization activities by the various conglutinin were detected. The focuses infected by Influenza viruses were detected by anti-influenza virus mouse monoclonal antibody, anti-mouse IgG goat serum, and peroxidase anti-peroxidase (PAP) staining system.

Neutralization activities by the recombinant conglutinin and the native conglutinin were shown in the following Table 3. Neutralization titer was shown as concentration to inhibit half (50%) of the infection.

TABLE 3

Neutralization Titer (μg/ml) of Recombinant Conglutinin and Native Conglutinin on Influenza A Viruses

| Virus | Recombinant Conglutinin | Native Conglutinin |
|---|---|---|
| A/Ibaraki/1/90(H3N2) | 0.22–0.63 | 0.08 |
| A/Suita/1/89(H1N1) | 0.31 | nt* |

*Not tested.

EXAMPLE 7

Viral Growth (Infection Spread) Inhibition Activities (1) Viruses

Figures 10A, 10B:
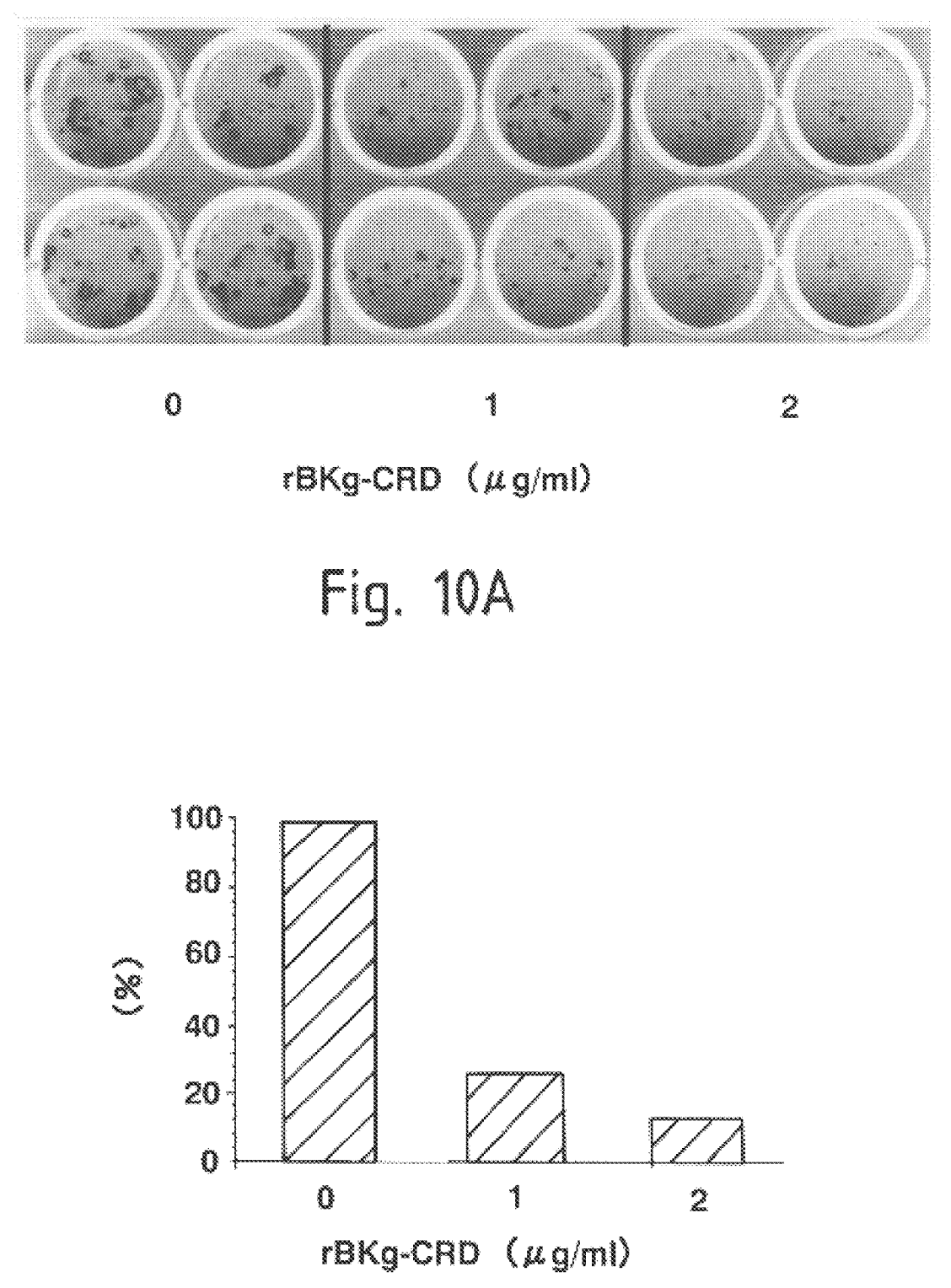
Figure 11A:
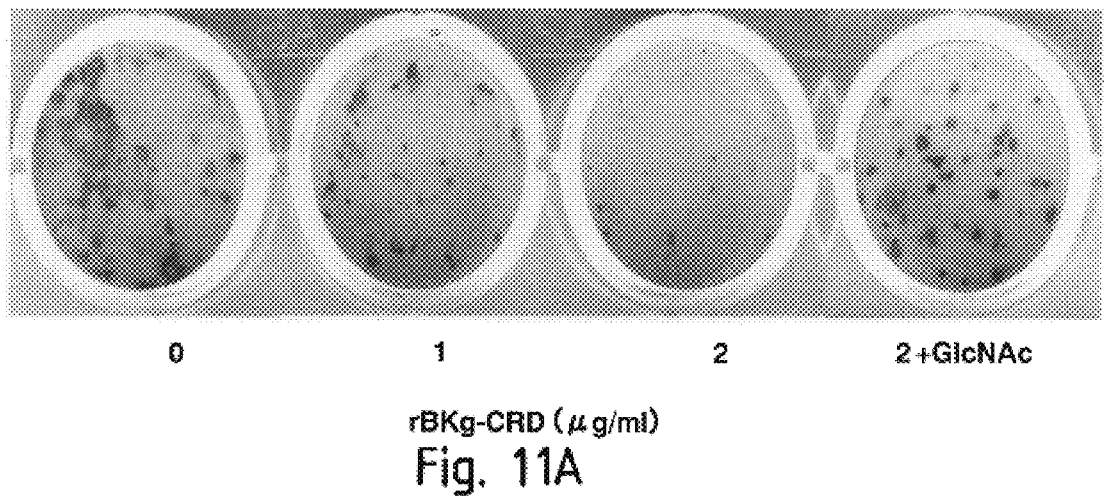
FIGS. 11A and 11B show viral growth (infection spread) inhibition activities on the recombinant conglutinin (rBKg-CRD)
Figure 11B:
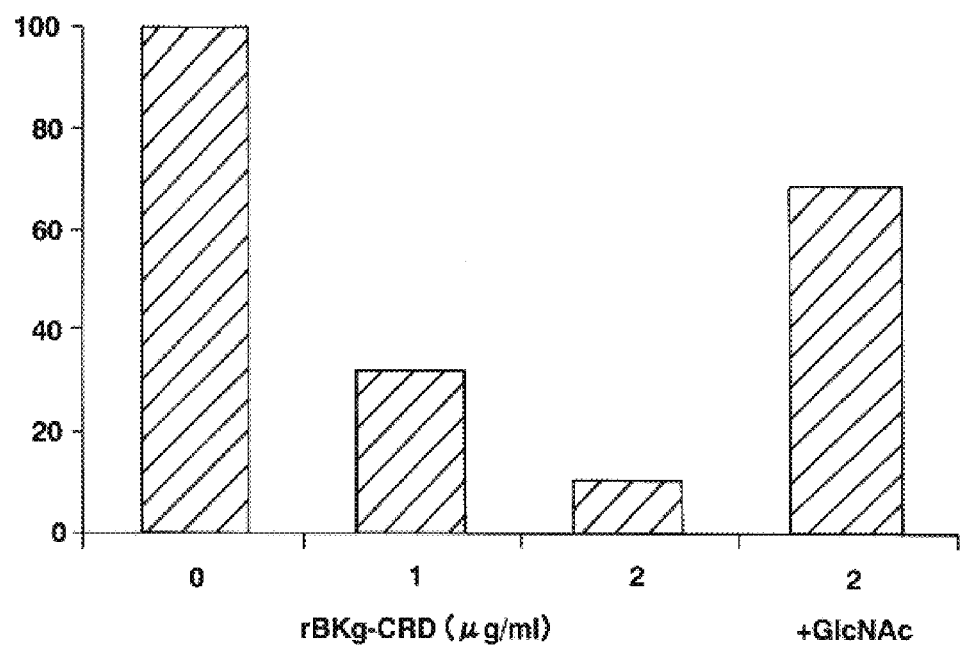

Influenza A virus, namely, Influenza A virus A/Ibaraki/1/90 (H3N2:Influenza A virus (A Hong Kong)) was used.
(2) Viral Growth (Infection Spread) Inhibition Activities Influenza viruses were inoculated onto Madin-Darby Canine Kidney (MDCK) cells in which the cells were cultured in 24-well microtiter plates with the Eagle MEM medium containing 10% fetal bovine serum. After washing the cells, they were incubated for three days in the growth medium for the influenza virus containing 0.5% tragacanth gum (Sigma) and any of 0, 1 and 2 μg/ml recombinant conglutinin. Like the procedure in the experiment on Neutralization Activities referred to in Example 6 (2), gross areas of the virus-infected focus were detected by PAP staining. Samples without the recombinant conglutinin were used as control. Results are shown in FIGS. 10A and 10B. Obviously from the results in FIGS. 10A and 10B, the recombinant conglutinin reduces the area of the infected focus in a dose dependent manner and inhibits the viral growth. This effect was inhibited by 2 μg/ml N-acetylglucosamine (GlcNAc) (FIG. 11).

EXAMPLE 8

Detection of Physiological Activities of Collectins

Figure 12A:
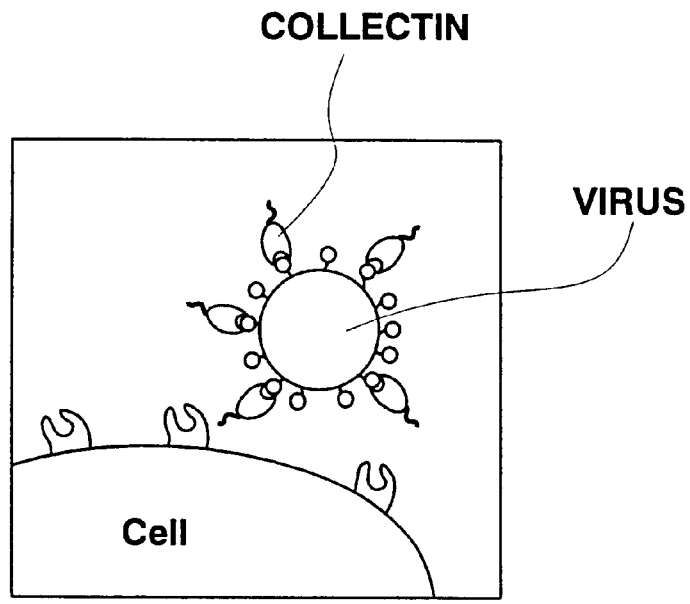
FIG. 12A and 12B illustratively show detection mechanism according to the conventional evaluation method on neutralization acitivites and the present invention.
Figure 12B:
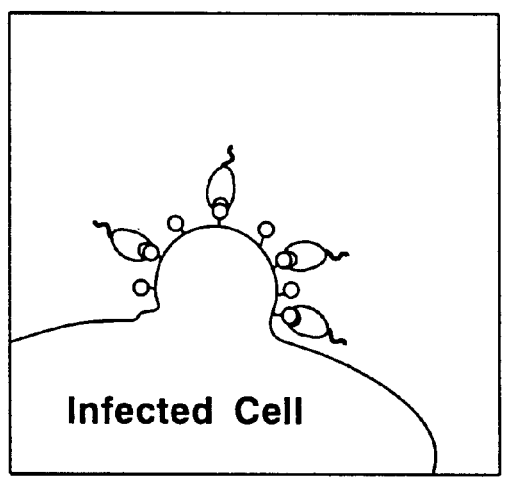

Detection method for the physiological activities of the collectins was constructed. The method is to evaluate the inhibition-effects on budding of the viruses from the cells preinfected with virus. The conventional method for detecting the physiological activities (e.g., detection on neutralization activities referred to in Example 6) comprises steps of contacting the collectins with viruses, infecting the cells with viruses of not binding to the collecting, and determining infection level by the binding activities between viruses and collectins, namely, neutralization activity (FIG. 12A). In contrast thereto, the present method detects the physiological activities of the collectins by evaluating the inhibition-effects on budding of the viruses from the cells preinfected with virus (FIG. 12B).

Physiological activities against Influenza A viruses were evaluated in accordance with the evaluation method on Hemagglutination Inhibition (HI) Activities according to Example 5, the evaluation method on Neutralization Activities according to Example 6, the evaluation on Hemagglutinin (HA) Activities by Western blotting, and the present method referred to in Example 7. Further, the neutralization activities against Influenza A viruses by the various collectins were also evaluated by the method referred to in Example 6. Results were shown in the following Tables 4 and 5.

TABLE 4

|  | HI Activity | Neutralization Activity | HA Binding | Present Method |
|---|---|---|---|---|
| Bovine Conglutinin | | | | |
| Native | + | + | + | − |
| Recombinant | + | + | + | + |
| hMBP | | | | |
| Native | + | − | − | + |
| Recombinant | − | − | − | − |
| Human Surfactant Protein (hSP-D) | | | | |
| Native | + | + | + | − |
| Recombinant | − | − | ± | − |

Abbreviation:
+, Presence of (Binding) Activity
−, Absence of (Binding) Activity

TABLE 5

|  | Neutralization Activity (Minimum Protein Concentration) |
|---|---|
| Human MBP | − (>5 μg/ml) |
| Rat MBP | ± (3 μg/ml) |
| Murine MBP | − (>8 μg/ml) |
| Rabbit MBP | + (0.07 μg/ml) |
| Bovine Conglutinin | + (0.09 μg/ml) | cf: Minimum Protein Concentration is necessary concentration to reduce infection scale down to 50% or less of control infected model.

Obviously from the results of Tables 4 and 5, the conventional method did not detect the neutralization activities against Influenza viruses by either the native hMBP or the recombinant hMBP. In contrast thereto, the present method surprising indicating the facts on HMBP that the native hMBP inhibited the viral growth (the infection spread). Then, inhibition effects on budding of viruses were evaluated on the native hMBP and the recombinant HMBP-CRD in accordance with the present method referred to in Example 7 by using, as a control, buffer solution without collectins. Results were shown in Table 6 below and FIG. 13.

TABLE 6

|  | Viral Growth Inhibition Activity (Minimum Protein Concentration) |
|---|---|
| native hMBP | + (0.05 μg/ml) |
| recombinant hMBP-CRD | − (>2.5 μg/ml) | cf: Minimum Protein Concentration is necessary concentration to reduce infection scale down to 50% or less of control infected model.

Figure 13:
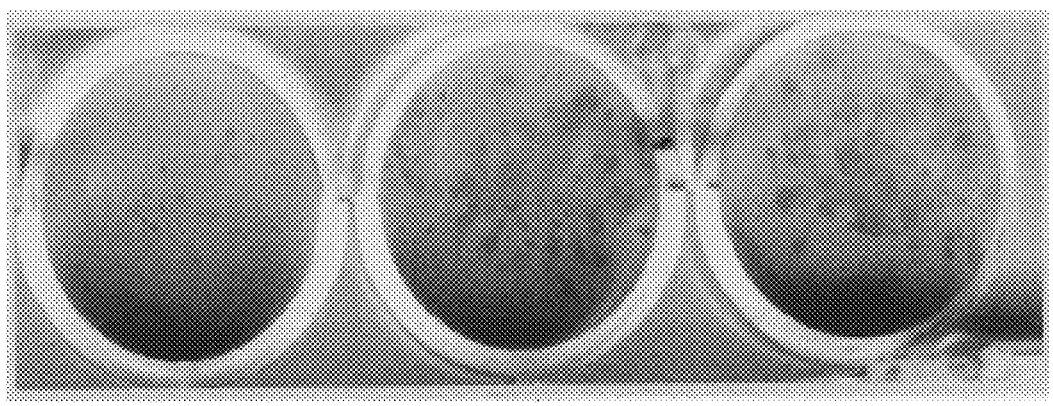
FIG. 13 shows viral growth inhibition by the human mannan-binding protein (hMBP)
Figure 14:
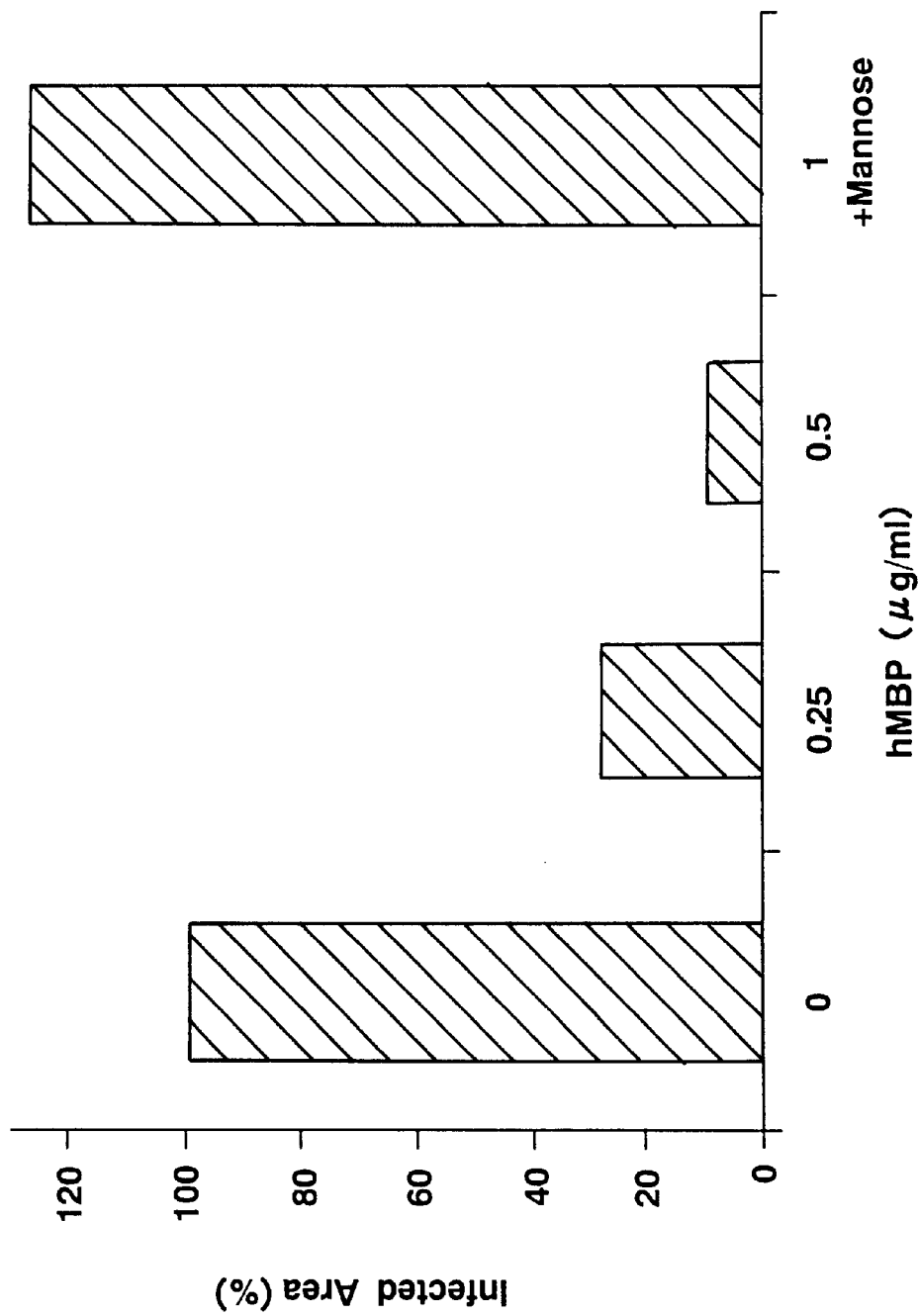
FIG. 14 is a graph showing viral growth inhibition by the human mannan-binding protein (hMBP)
Figure 15:
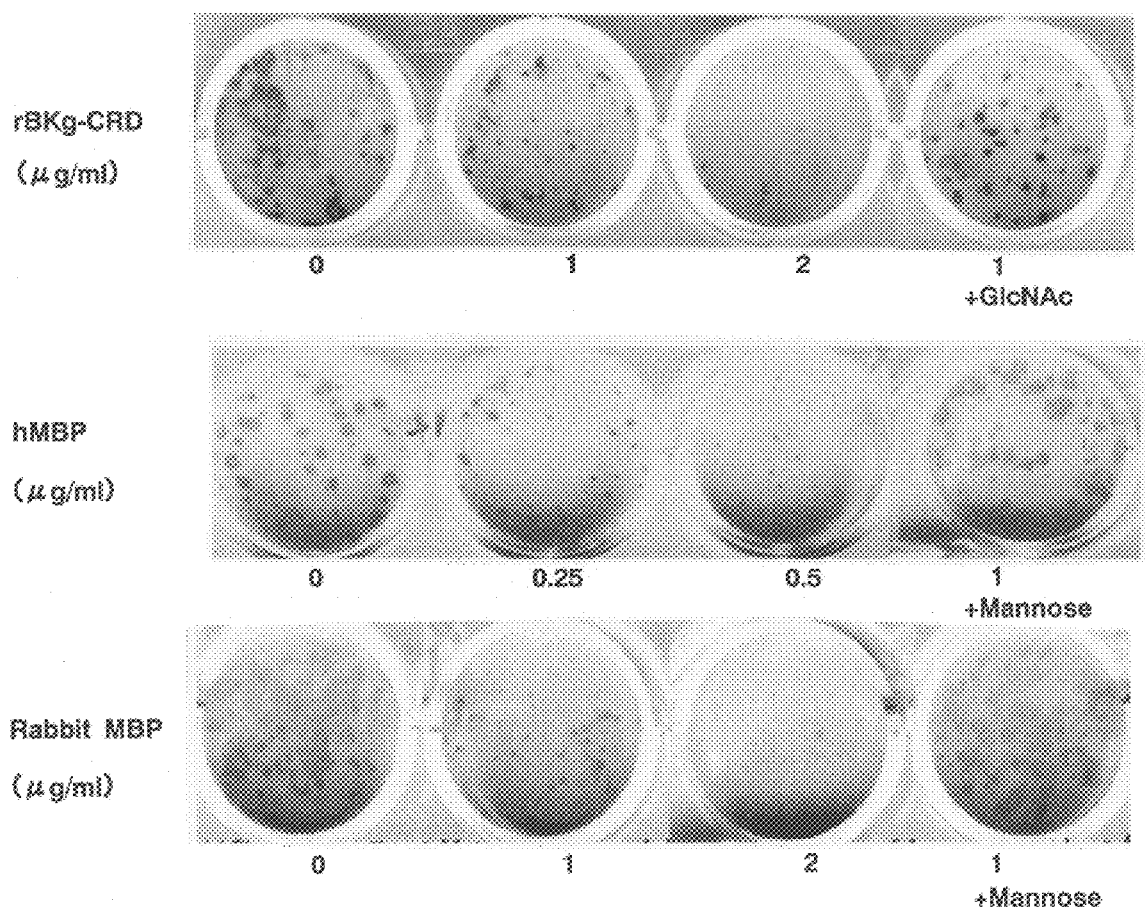
FIG. 15 shows viral growth inhibition by the recombinant conglutinin (rBKg-CRD), hMBP and rabbit MBP.

Results shown in Table 6 above and FIG. 13 demonstrated that the native hMBP inhibits growth (infection spread) of the viruses. The following experiments were performed to further demonstrate such new findings on the functions by HMBP. Influenza A viruses were inoculated onto Madin-Darby Canine Kidney (MDCK) cells in which the cells were cultured in 24-well microtiter plates with the Eagle MEM medium containing 10% fetal bovine serum. After washing the cells, they were incubated for three days in the growth medium for Influenza A viruses containing 0.5% tragacanth gum (Sigma) and any of 0, 0.25, and 0.5 μg/ml hMBP. Like the procedure in the experiment on Neutralization Activities referred to in Example 6 (2), gross areas of the virus-infected focus were detected by PAP staining. Samples containing 1

μg/ml N-acetylglucosamine (GlcNAc) were used as control. Results are shown in FIG. 14. Obviously from the results in FIG. 14, hMBP reduced the area of the infected focus in a dose-dependent manner and inhibited the viral growth. Such effects were also found in the recombinant conglutinin (rBKg-CRD), HMBP and rabbit MBP, when the physiological activities against Influenza A virus were evaluated along with the previously noted method (FIG. 15). In such evaluations, 1 μg/ml N-acetylglucosamine (GlcNAc) and 1 μg/ml mannose were employed as a control respectively for rBKg-CRD and for HMBP and rabbit MBP.

INDUSTRIAL APPLICABILITY

According to the present invention, means for artificially producing the large amount of the recombinant conglutinin can be realized wherein the recombinant conglutinin maintain the equivalent physiological activities to be expressed by the native conglutinin obtained with extremely low yield from the animal (bovine). Since the recombinant conglutinin of the present invention maintains the equivalent physiological activities to be expressed by the native conglutinin, its usefulness as a medicine will also be expected. Then, the recombinant conglutinin of the present invention is a part of the native conglutinin and have less molecular weight in comparison it with the native conglutinin, therefore, purification thereof will become smoother and advantages may offer in its manufacturing process.

In addition thereto, according to the present invention, novel method for detecting physiological activities of the collectins is also provided, then, physiological activities of the collectins can be evaluated from different aspects in combination with another conventional detection method. Further, the present detection method may provide a landmark to determine a preferable use of the collecting.

What is claimed is:

1. A method for detecting an anti-virus activity of calcium-dependent lectins comprising the steps of:
   (a) culturing cells in the presence of virus(es) to prepare virus(es)-infected cells,
   (b) presenting the virus(es)-infected cells in the presence or absence of a calcium-dependent lectin,
   (c) comparing gross area of virus(es)-infected focus formed in the presence of a calcium-dependent lectin with that formed in the absence of a calcium-dependent lectin, and
   (d) evaluating from the comparison results in step (c) an inhibition level by the calcium-dependent lectin on budding of virus in said infected cells,
      wherein the calcium-dependent lectin comprises an N-terminal region containing cysteine, a collagen-like region, a neck region and a carbohydrate recognition domain.

2. The method according to claim 1, wherein said calcium-dependent lectin is selected from the group consisting of mannan-binding protein (MBP), human mannan-binding protein (hMBP), conglutinin and recombinant conglutinin.

3. The method according to claim 1, wherein said virus is Influenza A virus.

4. The method for detecting the anti-virus activity according to claim 2 wherein said virus is Influenza A virus.

5. A method according to claim 1, further comprising the steps of:
   (e) selecting a calcium-dependent lectin determined to having budding inhibition anti-virus activity according to steps (a)–(d), and
   (f) formulating a composition by including, as an anti-virus agent of said composition, the calcium-dependent lectin having the detectable anti-virus activity.

6. The method of Claim wherein said calcium-dependent lectin is selected from the group consisting of mannan-binding protein, human mannan-binding protein or recombinant conglutinin.

7. The method of claim 5, wherein the virus is Influenza A virus.

8. A method according to claim 5 wherein the composition further includes a pharmaceutically acceptable carrier.

9. A method for detecting anti-virus activity of a calcium-dependent lectin, comprising the steps of:

(a) culturing cells in the presence of a virus to prepare virus-infected cells;

(b) culturing virus-infected cells from step (a) in the presence and absence of a calcium-dependent lectin;

(c) measuring virus-infected cells after culturing according to step (b); and (d) detecting anti-virus activity of the calcium-dependent lectin by comparing measurements of virus-infected cells from cells cultured in the presence and absence of the calcium dependent lectin, wherein anti-virus activity correlates with reduced virus-infected cells.

10. A method according to claim 9, wherein the measuring comprises determining the gross area of virus-infected focus in the cell culture.

11. A method according to claim 9, wherein the calcium-dependent lectin comprises an amino-terminal region containing cysteine, a collagen-like region, a neck region, and a carbohydrate recognition domain.

12. The method according to claim 9, wherein said virus is Influenza A virus.

* * * * *